United States Patent [19]

Kozlow

[11] 4,182,449
[45] Jan. 8, 1980

[54] ADHESIVE BANDAGE AND PACKAGE

[76] Inventor: William J. Kozlow, 200 Starcrest Dr., Apt. 60, Clearwater, Fla. 33515

[21] Appl. No.: 897,361

[22] Filed: Apr. 18, 1978

[51] Int. Cl.$^2$ .................. B65D 85/00; A61L 15/00
[52] U.S. Cl. .................................................. 206/441
[58] Field of Search ....................................... 206/441

[56] References Cited
U.S. PATENT DOCUMENTS

| 2,897,961 | 8/1959 | Bush | 206/441 |
|---|---|---|---|
| 2,924,331 | 2/1960 | Hoey | 206/441 |
| 2,946,435 | 7/1960 | Schladermundt et al. | 206/441 |

*Primary Examiner*—William T. Dixson, Jr.

*Attorney, Agent, or Firm*—Martha G. Pugh

[57] ABSTRACT

An adhesive bandage and package is provided wherein the package portion of the bandage serves as means by which the bandage may be applied to the wound without affecting sterility. More precisely, the adhesive bandage, having a backing, and a pad with a facing, and is partially covered by a first covering material covering just the pad and one adhesive coated area and serves as means to apply the bandage. The partially covered adhesive bandage is covered by a second suitable covering material that is heat, pressure, or ultrasonic sealed on the four sides parallel to the edges of the cover. One portion of the cover extends beyond the seal lines and serves as means for opening and applying the bandage.

6 Claims, 4 Drawing Figures

U.S. Patent     Jan. 8, 1980     4,182,449

ADHESIVE BANDAGE AND PACKAGE

BACKGROUND OF THE INVENTION

The adhesive bandages of prior art are packaged in packages which are separate from the bandages. They are usually equipped with a tearstring or some other means for opening the package. The package serves primarily to maintain sterility of the bandage. Upon removal of the bandage from the package one is to hold onto the unattached ends of the two release coated papers covering the pad and the adhesive portions of the bandage in order to apply the same to the wound.

My invention obviates the use of one release coated paper that is used to apply the adhesive bandage thus providing an economic advantage. It also eliminates the unnecessary separate handling of the adhesive bandage thereby minimizing the chance of contamination and the adhesive bandage is easier and faster to apply because the package is used as the means to apply the adhesive bandage.

PURPOSE OF THE INVENTION

The purpose of my invention is to provide an adhesive bandage and package in which conventionally used means to apply the adhesive bandage to a wound are eliminated, sterility maintained, and ease of handling is insured. Another purpose of my invention is to reduce the amount of material used in an adhesive bandage and package and thus obtain an economic gain.

SUMMARY OF THE INVENTION

The purposes and objectives of the present invention are accomplished in an adhesive bandage and package wherein the adhesive bandage is composed of a backing of a suitable material on one side of which is a pressure sensitive adhesive coating and centrally positioned thereon is a pad. A partial first cover of plastic or a release coated paper or foil is placed on the adhesive bandage just covering the pad and one adhesive coated area and is used together with the package as means to apply the bandage. There is placed over the covered bandage a plastic or a release coated paper or foil, completely covering the adhesive bandage and overlapping all edges. Said cover material is then heat, pressure or ultrasonic sealed beyond the periphery of the bandage and parallel to the cover edges. The portion of the cover extending beyond the seal serves as the means to hold and open the package, to apply the bandage. The purposes and objectives accomplished will be more readily understood from the detailed description that follows.

The adhesive bandage is covered with a second covering material consisting of two pieces substantially the same shape as the bandage but its dimensions are larger so that it extends somewhat beyond the edges of the bandage. The package is sealed on four edges parallel to the four edges of the adhesive bandage. There is a space between the inside edge of the package seal and the four edges of the bandage. The seal is formed by heat and pressure, pressure or ultrasonics. The package is longer on one end beyond the package seal thus forming the package peel tabs. The peel tabs have a straight shape and are on the end of the package nearest to the covered end portion of the adhesive bandage.

Figure 1:
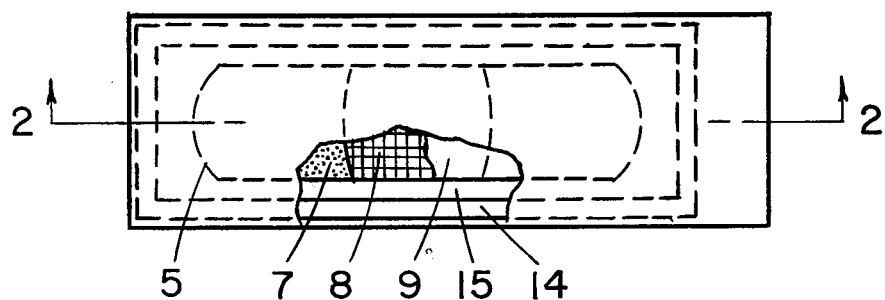
FIG. 1 is a plan view of the adhesive bandage and package. A portion of the adhesive bandage is covered by a first covering material covering the pad and extending to one end of the bandage and having the same width as the bandage.
Figure 2:
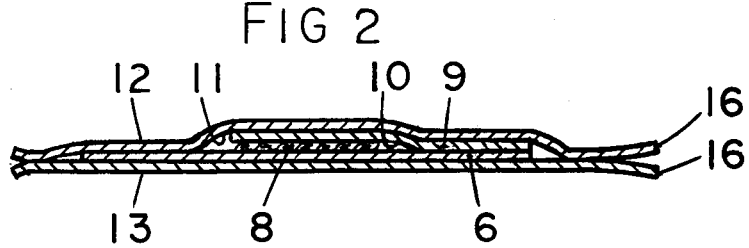

FIG. 2 is a cross section of the adhesive bandage and package shown in FIG. 1 taken along line 2.

Figure 3:
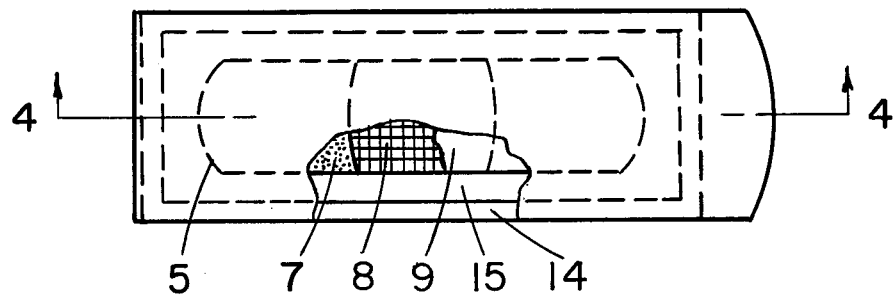

FIG. 3 is a plan view of the adhesive bandage and package. A portion of the adhesive bandage is covered by a first covering material covering the pad and extending to one end of the bandage and having the same width as the bandage. The adhesive bandage is covered with one piece of a second covering material folded to make both sides of the package. The covering material is substantially the same shape as the bandage but its dimensions are larger so that it extends somewhat beyond the edges of the bandage. The package is sealed on four edges parallel to the four edges of the adhesive bandage. There is a space between the inside edge of the package seal and the four edges of the bandage. The seal is formed by heat and pressure, pressure or ultrasonics. The package is longer on one end beyond the package seal thus forming the package peel tabs. The peel tabs have a curved shape and are on the end of the package nearest to the covered end portion of the adhesive bandage.

Figure 4:
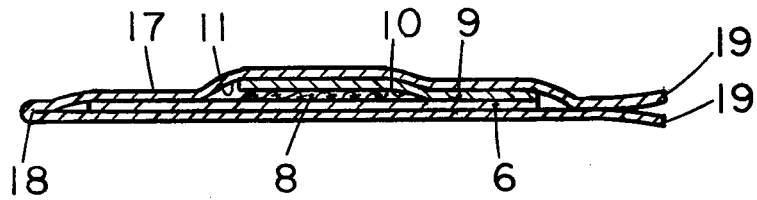

FIG. 4 is a cross section of the adhesive bandage and package shown in FIG. 3 taken along line 4.

DETAILED DESCRIPTION OF THE DRAWINGS

Referring to FIGS. 1, 2, 3 and 4 the adhesive bandage 5 has a perforated plastic backing 6, that is entirely coated on one face with a pressure sensitive adhesive 7. The bottom face of an absorbant pad 8 is stuck onto the adhesive 7 in the center of the adhesive face. The absorbant pad 8 has a wound release facing.

The adhesive bandage 5 is partially covered by cover 9 that covers the pad 8 and extends to one end of the backing 6 and is the same width as the backing 6. The cover 9 consists of paper, foil or similar material coated on one side with plastic 10 and the plastic side 10 faces pad 8. Alternatively the cover 9 can be of just plastic material.

The package in FIGS. 1 and 2 is made of two pieces of plastic, paper, foil or similar material. Package side 12 of paper or foil is coated on one face with plastic 11. The coated face 11 on package side 12 is placed on cover 9 on one side of the adhesive bandage 5. The other package side 13 is placed on the opposite side of the adhesive bandage.

The two pieces of the package 12 and 13 are sealed together by heat and pressure, pressure or ultrasonics. The package seal 14 is parallel to the four edges of the package and the four edges of the adhesive bandage 5. There is a space 15 between the inner edge of the package seal 14 and the four edges of the adhesive bandage 5.

Package sides 12 and 13 extend on one end of the package beyond the outside edge of the package seal 14 to form the package peel tabs 16. The peel tabs 16 have a straight shape and are on the end of the package nearest the cover 9 on the adhesive bandage 5.

In another embodiment of the invention as illustrated in FIGS. 3 and 4, the package 17 is formed from one piece of plastic, or from one piece of paper, foil or similiar material that is coated on one face with plastic 11 and folded 18 across its width to form both sides of the package 17 with the coated face 11 on the inside. The adhesive bandage 5 is placed between the coated faces 11 on package 17. The fold 18 on the package 17 is on the end of the package furthest from the cover 9 on the adhesive bandage 5. The package 17 is sealed together by heat and pressure, pressure or ultrasonics. The package seal 14 is parallel to the four edges of the package and the four edges of the adhesive bandage 5. There is a space 15 between the inner edge of the package seal 14 and the four edges of the adhesive bandage 5. The two sides of the package 17 extend on one end of the package beyond the outside edge of the package seal 14 to form the package peel tabs 19. The peel tabs 19 have a curved shape and are on the end of the package nearest the cover 9 on the adhesive bandage 5.

The package seal 14 in FIGS. 1 thru 4 is formed by heat and pressure or ultrasonics on plastic packages or packages that are coated on the inside in the seal area 14 with plastic.

The package seal 14 in FIGS. 1 thru 4 is formed by pressure on all packages coated on the inside in the seal area 14 with a pressure sensitive adhesive.

DESCRIPTION OF MATERIALS OF CONSTRUCTION

The adhesive bandage is made from materials customarily used to make an adhesive bandage. More specifically the adhesive bandage of the present invention can be made of materials as follows: In a conventionally used bandage there are three essential componants: a backing, adhesive, and a pad for contacting the wound. The backing is made from a soft plastic and is perforated throughout. The adhesive is a pressure sensitive material composed of a rubber or plastic compound, and the bandage pad is made from plastic foam, paper, cotton or gauze with or without a nonadherant plastic material on the top face for wound release.

The package or covering utilizes materials customarily used in making adhesive bandages and their wrappers. The package is made from paper or foil, with a plastic coating on one side, or from plastic. A package with a coating of a pressure sensitive adhesive compound of rubber or plastic in the seal area is closed by pressure and a package with a plastic coating in the seal area is closed by heat and pressure or ultrasonics.

What is claimed is:

1. An adhesive handage and package therefor comprising in combination:

an adhesive backing strip with a pressure-sensitive adhesive coating on one surface;

an absorbent pad centrally positioned on the adhesivecoated surface of said backing strip so that opposite ends of said adhesive-coated strip are substantially extended beyond opposite edges of said pad;

a single internal cover sheet having at least the same width as said adhesive backing strip, one of the ends of said internal cover sheet being sealed to one adhesive-coated end of said backing strip, the other free end of said internal cover sheet disposed to extend over in contact relation with said absorbent pad, completely covering and protecting said pad without being bonded thereto;

external covering means shaped similarly to said backing strip but dimensioned to extend beyond the edges thereof to provide narrow margins on the lateral edges and wider margins at opposite ends thereof, said external covering means being bonded at the edges to form a sterile sealed package for said adhesive bandage, including said backing strip, said absorbent pad and said internal cover sheet, whereby upon the opening of said package said internal cover sheet serves prior to removal as means for applying said adhesive bandage to a preselected surface.

2. The combination in accordance with claim 1 wherein a portion of said external covering means is sealed to the other adhesive-coated end of said backing strip, whereby upon the opening of said package said internal cover sheet and said external covering means together serve prior to removal as means attached to opposite ends of said backing strip for applying said adhesive bandage to a preselected surface.

3. The combination in accordance with either of claims 1 or 2 wherein at least that portion of the under surface said internal cover sheet in contact with said absorbent pad is plastic or plastic coated.

4. The combination in accordance with either of claims 1 or 2 wherein at least that portion of the under surface of said external covering means in contact with said internal cover sheet or said adhesive bandage is plastic coated.

5. The combination in accordance with either of claims 1 or 2 wherein said external covering means consists of two substantially symmetrical sheets disposed adjacent opposite surfaces of said adhesive bandage, being peripherally bonded at one end and along the lateral edges, and being bonded parallel to the other end to form a pair of peel tabs, wherein said adhesive bandage end, covered by said internal cover sheet is at the end adjacent said peel tabs.

6. The combination in accordance with either of claims 1 or 2 wherein said external covering means consists of a single sheet folded along its transverse axis adjacent one end of said adhesive bandage, being bonded along the lateral edges thereof, and bonded parallel to the opposite end thereof to form a pair of peel tabs, wherein said adhesive bandage end covered by said internal cover sheet, is at the end adjacent said peel tabs.

* * * * *